(12) United States Patent
Crowley

(10) Patent No.: US 7,986,764 B2
(45) Date of Patent: Jul. 26, 2011

(54) X-RAY LAMINOGRAPHY DEVICE, OBJECT IMAGING SYSTEM, AND METHOD FOR OPERATING A SECURITY SYSTEM

(75) Inventor: Christopher W. Crowley, San Diego, CA (US)

(73) Assignee: Morpho Detection, Inc., Newark, CA (US)

( * ) Notice: Subject to any disclaimer, the term of this patent is extended or adjusted under 35 U.S.C. 154(b) by 33 days.

(21) Appl. No.: 12/329,990

(22) Filed: Dec. 8, 2008

(65) Prior Publication Data

US 2010/0142672 A1 Jun. 10, 2010

(51) Int. Cl.
*G01N 23/04* (2006.01)
*G01N 23/083* (2006.01)
*H05G 1/02* (2006.01)
*H05G 1/60* (2006.01)

(52) U.S. Cl. ............... 378/23; 378/21; 378/22; 378/27; 378/196; 378/197

(58) Field of Classification Search ............... 378/9, 20, 378/21, 22, 23, 24, 25, 26, 27, 196, 197, 378/209
See application file for complete search history.

(56) References Cited

U.S. PATENT DOCUMENTS

| | | | |
|---|---|---|---|
| 4,511,799 A | 4/1985 | Bjorkholm | |
| 5,182,764 A * | 1/1993 | Peschmann et al. | 378/57 |
| 5,259,012 A | 11/1993 | Baker et al. | |
| 5,442,672 A | 8/1995 | Bjorkholm et al. | |
| 5,583,904 A * | 12/1996 | Adams | 378/22 |
| 6,370,223 B1 * | 4/2002 | Gleason et al. | 378/58 |
| 6,411,674 B1 * | 6/2002 | Oikawa | 378/21 |
| 6,430,255 B2 * | 8/2002 | Fenkart et al. | 378/57 |
| 6,618,464 B2 * | 9/2003 | Mizobuchi et al. | 378/55 |
| 6,668,403 B2 * | 12/2003 | Seufert | 5/601 |
| 6,748,046 B2 | 6/2004 | Thayer | |
| 6,763,083 B2 * | 7/2004 | Fernandez | 378/41 |
| 6,856,667 B2 * | 2/2005 | Ellengogen | 378/57 |
| 6,977,985 B2 | 12/2005 | Bohn et al. | |
| 7,060,981 B2 * | 6/2006 | Retterath et al. | 250/359.1 |
| 7,108,421 B2 * | 9/2006 | Gregerson et al. | 378/197 |
| 7,245,698 B2 * | 7/2007 | Pang et al. | 378/65 |
| 7,263,157 B2 * | 8/2007 | Bruder et al. | 378/19 |
| 2008/0170662 A1 | 7/2008 | Reinhold | |

FOREIGN PATENT DOCUMENTS

EP 0355128 B1 2/1990
WO 02088689 A2 11/2002

\* cited by examiner

*Primary Examiner* — Allen C. Ho
(74) *Attorney, Agent, or Firm* — Armstrong Teasdale LLP

(57) ABSTRACT

An x-ray laminography device includes at least one x-ray detector and at least one x-ray source coupled in coordinated traversal with the at least one x-ray detector. The at least one x-ray source is configured to generate and transmit x-rays. The at least one x-ray detector and the at least one x-ray source traverse an at least partially radial travel path in unison about an object such that the object is illuminated with x-rays from a plurality of oblique radial angles defined between the at least one x-ray source and the object.

16 Claims, 4 Drawing Sheets

X-RAY LAMINOGRAPHY DEVICE, OBJECT IMAGING SYSTEM, AND METHOD FOR OPERATING A SECURITY SYSTEM

BACKGROUND OF THE INVENTION

1. Field of the Invention

The embodiments described herein relate generally to operating security systems and, more particularly, to an x-ray laminography device and a method for operating a security system having such x-ray laminography device.

2. Description of Prior/Related Art

Many known security systems include an object imaging system that includes either a single-view or a multi-view x-ray screening device. Such known single-view x-ray screening devices include a single x-ray source to generate a single x-ray beam having one or more energy levels. These screening devices also include a single x-ray detector that receives at least a portion of the x-ray stream subsequent to interaction with a piece of baggage. The single-view x-ray screening device generates two-dimensional (2D) images of varying quality and accuracy. In contrast, known multi-view x-ray screening devices typically provide both enhanced quality and accuracy.

At least some of the aforementioned known multi-view screening devices use a plurality of x-ray sources to generate a plurality of x-ray beams, wherein each beam is at least partially generated with one or more x-ray energy levels differing from each other beam. Some of such known screening devices also include a plurality of x-ray detectors configured to receive at least a portion of the x-ray beams subsequent to interaction with a piece of baggage. Moreover, some of these screening devices include x-ray source and x-ray detector pairs at approximately 90° to each other. A first x-ray source/detector pair is positioned directly over/under the baggage and a second x-ray source/detector pair is positioned at opposite sides of the baggage. Such multi-view x-ray screening device also generates either a two-dimensional (2D) or three-dimensional (3D) image of superior quality with respect to the single-view x-ray devices. These known multi-view screening devices perform well for general baggage screening. They are typically more accurate with respect to differentiating contraband substances from other substances, thereby reducing a need for manual inspections of baggage items. However, such known multi-view x-ray screening devices are not as effective for baggage items with a physically lower-profile, such as a laptop computer within a case.

Therefore, since most security systems, such as airport security and baggage screening systems, include known single-view and multi-view screening systems, screening procedures typically require individuals to remove laptop computers from their associated cases and place them on a conveyor belt. The removal is necessitated by the substantially flat, low-profile that is associated with laptop computers and their cases. The low-profile typically confounds larger screening systems with geometric features more suitably configured for general baggage screening. The additional burden of removing laptop computers from the cases during the screening process may provide frequent travelers a cumbersome annoyance, wherein contents may spill from the cases, some articles may get lost, and the laptop computer may be inadvertently handled roughly. Such an annoyance is compounded by the fact that individuals may also taking off their shoes at the same time. Moreover, each additional activity performed by, for example, a plane passenger, takes a finite period of time to complete with an additional burden for security screening personnel to provide sufficient oversight of such activities.

Object imaging systems that include computed tomography (CT) scanning technology with 3D reconstruction features may offer future opportunities for eliminating the need to remove substantially flat, low-profile objects from their cases. However, most known CT-based scanning systems are too expensive and too large to deploy at typical security screening stations, and are therefore impractical for eliminating laptop computer screening issues. Accordingly, it is desirable to have an object imaging system having a relatively small footprint that effectively and efficiently scans substantially flat, low-profile items, such as laptop computers, while such items are residing within their packaging and/or encasements.

BRIEF DESCRIPTION OF THE INVENTION

In one aspect, an x-ray laminography device is provided. The x-ray laminography device includes at least one x-ray detector and at least one x-ray source coupled in coordinated traversal with the at least one x-ray detector. The at least one x-ray source is configured to generate and transmit x-rays. The at least one x-ray detector and the at least one x-ray source traverse an at least partially radial travel path in unison about an object such that the object is illuminated with x-rays from a plurality of oblique radial angles defined between the at least one x-ray source and the object.

In another aspect, an object imaging system is provided. The object imaging system includes at least one processing system. The object imaging system also includes a traveling belt operatively coupled to the at least one processing system. The object imaging system further includes an x-ray laminography device that includes at least one x-ray detector coupled to the at least one processing system. The x-ray laminography device also includes at least one x-ray source coupled in coordinated traversal with the at least one x-ray detector. The at least one x-ray source is configured to generate and transmit x-rays. The at least one x-ray detector and the at least one x-ray source traverse an at least partially radial travel path in unison about an object such that the object is illuminated with x-rays from a plurality of oblique radial angles defined between the at least one x-ray source and the object.

In still another aspect, a method for operating a security system is provided. The method includes directing coordinated traversal of at least one x-ray detector and at least one x-ray source about an object along a travel path at least partially defined radially about the object. The method also includes illuminating the object with x-rays directed from a plurality of oblique radial angles defined between the at least one x-ray source and the object.

Embodiments of the method and device described herein facilitate effective and efficient operation of a security system by decreasing a need to have substantially flat, low-profile items, such as laptop computers, removed from their encasements, such as laptop cases, at security checkpoints. The method and x-ray laminography device described herein may result in substantially reducing the need for individuals to remove their laptop computers from the associated cases at the security checkpoints. Scanning such laptop computers from a plurality of oblique angles with the x-ray laminography device described herein, while such computers are residing within their associated cases, and then generating and displaying a three-dimensional (3D) image of the contents, facilitates decreasing a scanning time of each item and decreasing oversight efforts expended by screening agencies and individuals.

BRIEF DESCRIPTION OF THE DRAWINGS

FIG. 1 is a schematic view of an exemplary object imaging system including an exemplary x-ray laminography device.

FIG. 2 is a flow chart of an exemplary method of operating the security system shown in FIG. 1.

FIG. 3 is a schematic view of an alternative object imaging system including an alternative x-ray laminography device.

FIG. 4 is a schematic view of another alternative object imaging system including another alternative x-ray laminography device.

DETAILED DESCRIPTION OF THE INVENTION

Figure 1:
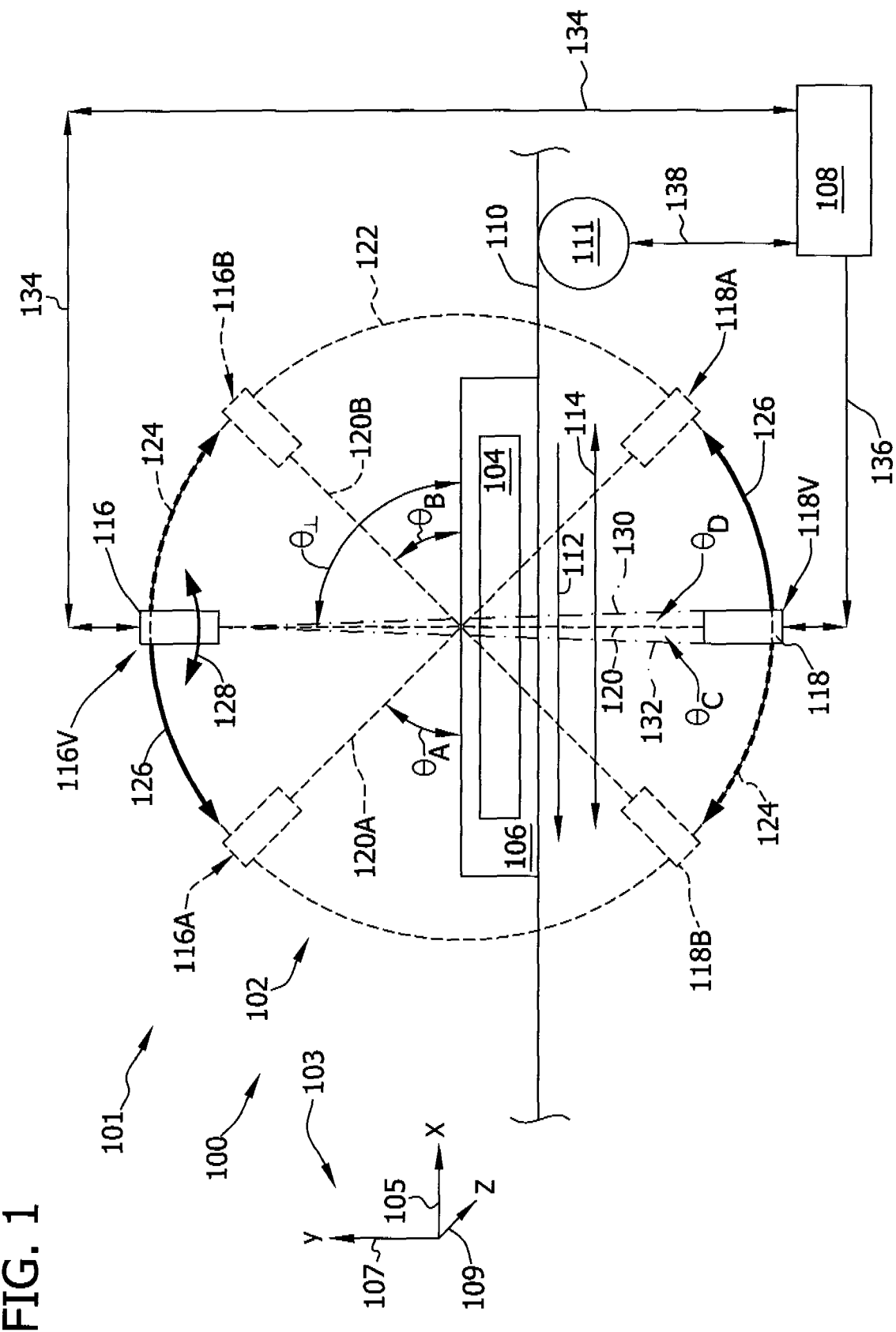
FIGS. 1-4 show exemplary and alternative embodiments of the devices, systems, and methods described herein.

The method and x-ray laminography device described herein facilitate effective and efficient operation of security systems. The security systems include an object imaging system that includes an x-ray laminography device that scans substantially flat, low-profile items, such as, but not limited to, laptop computers. Such scanning is performed from a plurality of oblique scanning angles without necessitating removal of the computer from its case. The x-ray laminography device subsequently generates and displays a three-dimensional (3D) image of the contents of the laptop computer while residing within the associated case. Therefore, the x-ray laminography device decreases a need to have laptop computers removed from their cases at security checkpoints, thereby decreasing oversight efforts of screening agencies and individuals and the time per unit item expended. Moreover, the x-ray laminography device has a sufficiently small footprint to facilitate inclusion within many existing security checkpoints.

A technical effect of the x-ray laminography device and method described herein is to provide the users of the object imaging system and security system described herein with features arranged so that substantially flat, low-profile items, such as laptop computers, may be scanned effectively and efficiently without taking the laptop computer out of its associated case. This ability to scan substantially flat, low-profile items within their encasements facilitates moving individuals through security checkpoints quickly and easily. Embodiments of object imaging systems described herein include an x-ray source and x-ray detector that rotate about the item to be scanned in unison. Also, embodiments of the object imaging systems described herein include one or more x-ray sources and one or more x-ray detectors that rotate in unison with each other about the item to be scanned, thereby further facilitating security system operation.

At least one embodiment of the present invention is described below in reference to its application in connection with and operation of a security system for inspection of items at security checkpoints. However, it should be apparent to those skilled in the art and guided by the teachings provided herein that embodiments of the invention are likewise applicable to any suitable inspection system configured to perform inspections of substantially flat, low-profile items.

At least some of the components of the object imaging systems and security systems described herein include at least one processor and a memory, at least one processor input channel, and at least one processor output channel. As used herein, the term processor is not limited to just those integrated circuits referred to in the art as a computer, but broadly refers to a microcontroller, a microcomputer, a programmable logic controller (PLC), an application specific integrated circuit, and other programmable circuits, and these terms are used interchangeably herein. In the embodiments described herein, memory may include, without limitation, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may include, without limitation, computer peripherals associated with an operator interface such as a mouse and a keyboard. Alternatively, other computer peripherals may also be used that may include, for example, without limitation, a scanner. Furthermore, in the exemplary embodiment, additional output channels may include, without limitation, an operator interface monitor.

The processors as described herein process information transmitted from a plurality of electrical and electronic components that may include, without limitation, security system inspection equipment and object imaging systems that include x-ray laminography devices. Such processors may be physically located in, for example, the x-ray laminography devices, desktop computers, laptop computers, PLC cabinets, and/or distributed control system (DCS) cabinets. RAM and storage devices store and transfer information and instructions to be executed by the processor. RAM and storage devices can also be used to store and provide temporary variables, static (i.e., non-changing) information and instructions, or other intermediate information to the processors during execution of instructions by the processors. Instructions that are executed include, without limitation, resident security system control commands. The execution of sequences of instructions is not limited to any specific combination of hardware circuitry and software instructions.

FIG. 1 is a schematic view of an exemplary object imaging system 100 including an exemplary x-ray laminography device 102. In the exemplary embodiment, object imaging system 100 is integrated within a larger, more comprehensive security system 101.

Security system 101 is configured to operate at security checkpoints (not shown) and security system 101 includes other systems (not shown) such as, large x-ray-type devices (not shown) configured to scan larger-profile items, such as suitcases and shipping crates.

In the exemplary embodiment, object imaging system 100 is configured to inspect substantially flat, low-profile items that include, without limitation, laptop computers 104 that may be carried by individuals (not shown) and in their associated cases 106. Moreover, in the exemplary embodiment, object imaging system 100 includes a processing system 108. Processing system 108 includes sufficient information technology resources to record, analyze, synthesize, and reconstruct data collected. The information technology resources may include, without limitation, processing, memory, and input/output (I/O) resources as described above. Processing system 108 also includes sufficient programming to use at least one of a variety of methods of reconstruction including, but not limited to, algebraic reconstruction techniques. Such reconstruction techniques facilitate the technical effect of forming a three-dimensional (3D) image substantially representative of laptop computer 104 and case 106 and contents therein.

Processing system 108 may include equipment (not shown) such as, but not limited to, printers, desk top computers, laptop computers, servers, and hand-held devices, such as personal data assistants (PDAs), that perform system and network functions that include, but are not limited to, diagnostics, reporting, technical support, configuration, system and network security, and communications.

As described above, in the exemplary embodiment, object imaging system 100 includes processing system 108 and the resources of processing system 108 are dedicated to object imaging system 100. Alternatively, processing system 108 may be a part of and/or integrated within a larger processing system (not shown) associated with a remainder (not shown) of security system 101. That is, processing system 108 may be coupled with other systems and networks (neither shown) via a local area network (LAN) or Wide Area Network (WAN) (neither shown). Moreover, processing system 108 may be coupled with other systems and networks including, but not limited to, a remote central monitoring station via the Internet and/or a radio communications link (neither shown), wherein any network configuration using any communication coupling may be used. Alternatively, in contrast to being a portion of a larger system, processing system 108 may be solely associated with x-ray laminography device 102.

For illustration and perspective, FIG. 1 shows a coordinate system 103 that includes an x-axis 105 (substantially representing a horizontal, longitudinal, or lengthwise dimension), a y-axis 107 (substantially representing a vertical dimension), and a z-axis 109 (substantially representing a depth, traverse, or widthwise dimension). Each axis is orthogonal to each other axis.

Object imaging system 100 also includes a traveling belt 110 and belt drive apparatus 111. Belt drive apparatus 111 is operatively coupled in motive operation of belt 110. Apparatus 111 includes at least one of an electric drive motor, a hydraulic drive motor, a pneumatic motor, and/or a gearbox (not shown), and/or any other suitable device. Apparatus 111 drives belt 110 primarily in the substantially horizontal, longitudinal, or lengthwise direction as indicated by a direction arrow 112 substantially parallel to x-axis 105. Apparatus 111 is reversible such that belt 110 also travels with an oscillating motion as indicated by a bidirectional arrow 114, that is also substantially parallel to x-axis 105. That is, apparatus 111 drives belt 110 to travel in a direction reverse to that of arrow 112 and then drives belt 110 to travel in the direction of arrow 112 to facilitate multiple scans by x-ray laminography device 102.

In the exemplary embodiment, x-ray laminography device 102 includes at least one x-ray source 116 and an array of x-ray detectors 118. X-ray source 116 and array of x-ray detectors 118 may include any suitable devices known in the art. X-ray source 116 is configured to generate and transmit an x-ray beam (not shown) and array of x-ray detectors 118 is configured to receive at least a portion of the beam. In the exemplary embodiment, array of x-ray detectors 118 includes a transverse orientation with respect to bidirectional arrow 114. X-ray source 116 and array of x-ray detectors 118 define a first beam path 120 therebetween. Generation, transmission, and receipt of the x-ray beam are referred to herein as a "shot". Moreover, x-ray source 116 is initially positioned in a first, or vertical x-ray source position 116V and array of x-ray detectors 118 is initially positioned in a first, or vertical array of x-ray detectors position 118V wherein first beam path 120 defines a radial right angle $\theta\perp$.

In the exemplary embodiment, x-ray source 116 and array of x-ray detectors 118 are coupled in coordinated, joint traversal about at least a portion of a substantially circular, or a 360° travel path 122 defined by such joint traversal in an x-y plane (not shown) defined substantially solely by x-axis 105 and y-axis 107. More specifically, in the exemplary embodiment, x-ray source 116 and array of x-ray detectors 118 travel in unison in a clockwise direction as indicated by clockwise arrows 124 and a counter-clockwise direction as indicated by counter-clockwise arrows 126. Such travel may be facilitated by suitable devices known in the art including, without limitation, robotic/mechanical arms, tracks/rails, and motors (not shown).

In the exemplary embodiment, travel represented by arrows 124 and 126 is approximately 45° in each direction from the directly vertical position as shown in FIG. 1. Alternatively, travel path 122 has any shape that enables operation of object imaging system 100 and x-ray laminography device 102 as described herein, including, without limitation, a parabolic shape. Also, alternatively, travel for any arcual portion of travel path 122 that enables operation of object imaging system 100 and x-ray laminography device 102 as described herein may be used. Further, alternatively, travel path 122 is defined by such traversal in a plane (not shown) that is at least partially defined by x-axis 105, y-axis 107, and z-axis 109 in any combination and proportion that enables operation of object imaging system 100 and x-ray laminography device 102 as described herein.

Moreover, x-ray source 116 and array of x-ray detectors 118 travel along circular travel path 122 such that beam path 120 substantially extends from x-ray source 116 to array of x-ray detectors 118 regardless of their position about path 122. More specifically, x-ray source 116 travels along circular path 122 per counter-clockwise arrow 126 to a second x-ray source position 116A and array of x-ray detectors 118 travels along circular travel path 122 per counter-clockwise arrow 126 to a second array of x-ray detectors position 118A such that a first oblique radial angle $\theta_A$ between x-ray source 116 and case 106, as shown in FIG. 1, at least partially defines a second beam path 120A. In one embodiment, case 106 is a laptop bag or briefcase. Also, x-ray source 116 travels along circular path 122 per clockwise arrow 124 to a third x-ray source position 116B and array of x-ray detectors 118 travels along circular travel path 122 per clockwise arrow 124 to a third array of x-ray detectors position 118B such that a second oblique radial angle $\theta_B$ between x-ray source 116 and case 106, as shown in FIG. 1, at least partially defines a third beam path 120B.

Further, x-ray source 116 is coupled to a pivoting device (not shown) such that pivoting action of x-ray source 116 defines an arc 128, that in the exemplary embodiment, is defined in an angular range of approximately 2° to 10° in the x-y plane, that is, at least partially in the longitudinal direction parallel with bidirectional arrow 114. Alternatively, arc 128 is defined with any angular range that enables operation of object imaging system 100 and x-ray laminography device 102 as described herein. Such pivoting action subsequently defines a plurality of beam paths that includes, for example, a fourth beam path 130 and a fifth beam path 132, also in the longitudinal direction. Alternatively, such pivoting action defines arc 128 in a plane (not shown) that is at least partially defined by x-axis 105, y-axis 107, and z-axis 109 in any combination and proportion that enables operation of object imaging system 100 and x-ray laminography device 102 as described herein.

Moreover, such pivoting action of x-ray source 116 about arc 128 is performed within the detection constraints of array of x-ray detectors 118. That is, x-ray source 116 pivots along arc 128 such that beam paths 130 and 132 substantially extend between x-ray source 116 and x-ray detectors 118 regardless of a position of x-ray source 116 and a position of array of x-ray detectors 118 about path 122. Such pivoting action about arc 128 in conjunction with the circular traversal about path 122 facilitates greater flexibility of scanning, or illuminating case 106 and laptop computer 104 at varying radially oblique angles that include, but are not limited to, a third oblique radial angle $\theta_C$ and a fourth oblique radial angle $\theta_D$. Angles $\theta_C$ and $\theta_D$ are at least partially defined by x-ray source 116 and laptop computer 104 and case 106, and both angles $\theta_C$ and $\theta_D$ are at least partially defined by arc 128. Such pivoting action facilitates greater scanning resolution as discussed further below.

Further, such pivoting action of x-ray source 116 facilitates reducing traversing movements of x-ray source 116 about arrows 124 and 126 and oscillating travel of belt 110 via apparatus 111, thereby facilitating extending an expected operational lifetime of those components associated with such traversing and oscillating and decreasing a period of time associated with scanning of computer 104 and case 106. Moreover, reducing such traversing and oscillating facilitates use of smaller components, thereby facilitating decreasing a footprint of object imaging system 100 and x-ray laminography device 102.

In the exemplary embodiment, processing system 108 is coupled with components of object imaging system 100 including x-ray source 116, array of x-ray detectors 118, and belt drive apparatus 111 via communication conduits 134, 136, and 138, respectively. Processing system 108 substantially controls and coordinates operation of x-ray source 116, x-ray detectors 118, and apparatus 111 to illuminate laptop computer 104 and case 106 with the x-ray beam as described herein.

Figure 2:
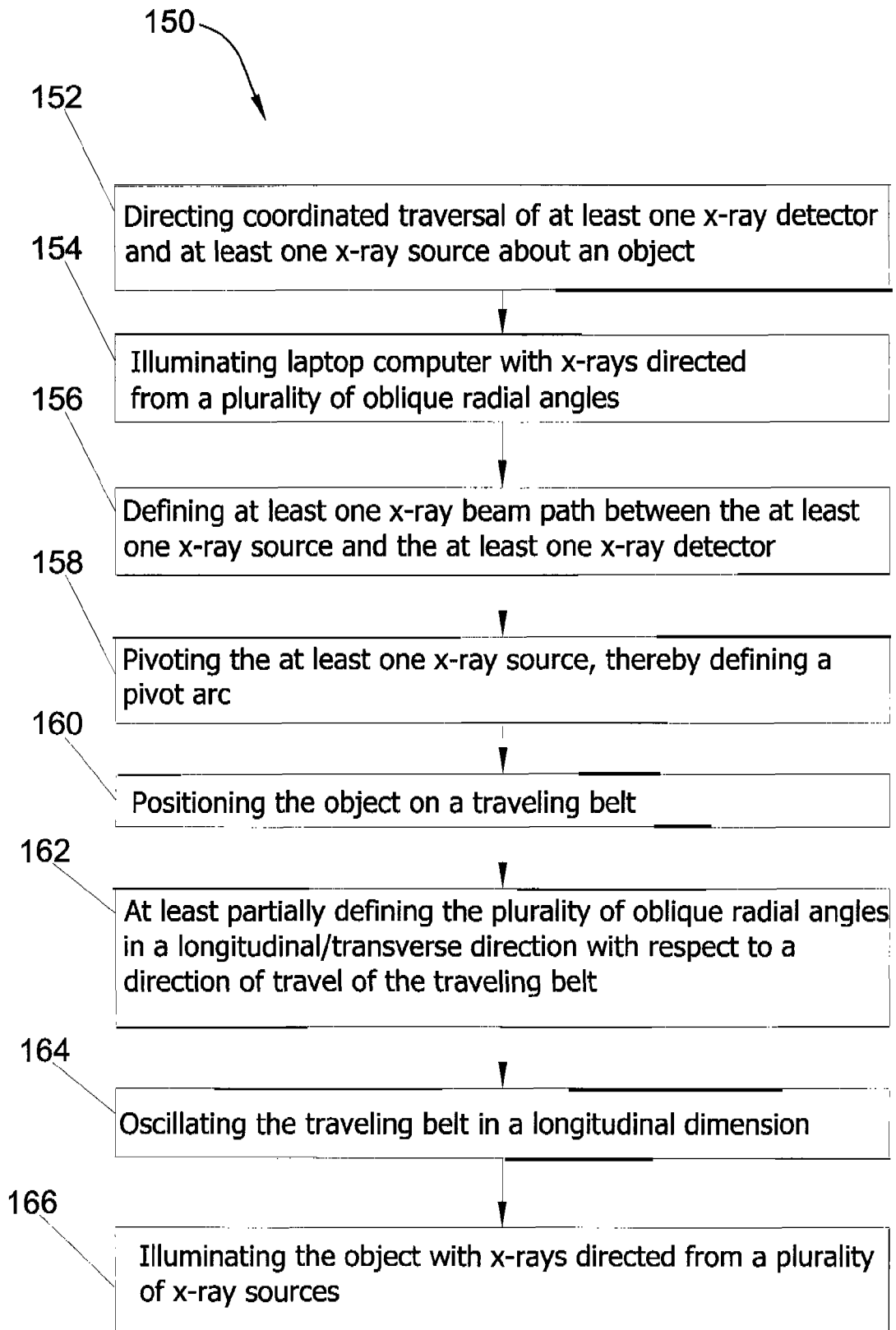

FIG. 2 is a flow chart of an exemplary method 150 of operating security system 101 (shown in FIG. 1). Exemplary method 150 of operating security system 101 includes directing 152 coordinated traversal of at least one x-ray detector 118 and at least one x-ray source 116 about an object, such as laptop computer 104, along a travel path 122 at least partially defined radially about laptop computer 104. Method 150 also includes illuminating 154 laptop computer 104 with x-rays directed from a plurality of oblique radial angles $\theta_A$ and $\theta_B$ defined between x-ray source 116 and laptop computer 104.

Method 150 further includes defining 156 at least one x-ray beam path 120, 120A, and 120B between at least one x-ray source 116 and at least one x-ray detector 118, wherein the at least one x-ray beam path 120, 120A, and 120B is at least partially defined by at least one of plurality of oblique radial angles $\theta_A$ and $\theta_B$. Method 150 also includes pivoting 158 at least one x-ray source 116, thereby defining pivot arc 128, wherein the at least one x-ray beam path includes plurality of x-ray beam paths 130 and 132 at least partially defined by the pivot arc 128.

Method 150 also includes positioning 160 laptop computer 104 on traveling belt 110. Method 150 further includes at least partially defining 162 plurality of oblique radial angles $\theta_A$, $\theta_B$, $\theta_C$, and $\theta_D$ in a longitudinal direction with respect to direction of travel 114 of traveling belt 110. Moreover, in method 150, positioning 160 laptop computer 104 on traveling belt 110 comprises oscillating 164 traveling belt 110 in a longitudinal dimension, or x-axis 105.

During operation, x-ray detector 118 moves in unison with x-ray source 116 about an arcual portion of circular travel path 122 such that an x-ray beam is transmitted from x-ray source 116 to x-ray detector 118 along beam path 120. X-ray detector 118 and x-ray source 116 traverse path 122 in predetermined arcs in the direction of arrow 124 and/or arrow 126. X-ray detector 118 and x-ray source 116 are temporarily positioned at predetermined stationary positions that include, but are not limited to, positions 118V, 118A, and 118B and 116V, 116A, and 116B, respectively, along path 122 and the associated x-ray beams are generated at each position to illuminate laptop computer 104 and case 106 with as many "shots" as necessary to facilitate 3D reconstruction of laptop computer 104, case 106, and any contents within laptop computer 104 and/or case 106 via processing system 108. For example, in one embodiment, shots are be taken at 9° increments along the 90° arc to generate 10 shots of computer 104 and case 106 that are subsequently reconstructed to form a 3D image as described above.

Also, during operation, x-ray source 116 tilts about arc 128 to provide greater variety and flexibility in shot angles that include, but are not limited to, combinations of a plurality of oblique radial angles that include $\theta_A$, $\theta_B$, $\theta_C$, and $\theta_D$ by generating x-ray beams that are transmitted via a plurality of beam paths 120, 120A, 120B, 130, 132. Moreover, during operation, belt 110 is positioned via belt drive apparatus 111. Belt 110 may be held stationary through a period of time for one or more shots of computer 104 and case 106 and, alternatively, belt 110 may be positioned for each shot of computer 104 and case 106.

Further, during operation, coordination of belt 110, position of x-ray source 116 and x-ray detector 118, and a tilt of x-ray source 116 are controlled automatically by processing system 108. Alternatively, all positioning and shooting is controlled manually by an operator (not shown). Also, alternatively, operation of object imaging system 100 is performed through a combination of automatic and manual positioning and shooting.

Figure 3:
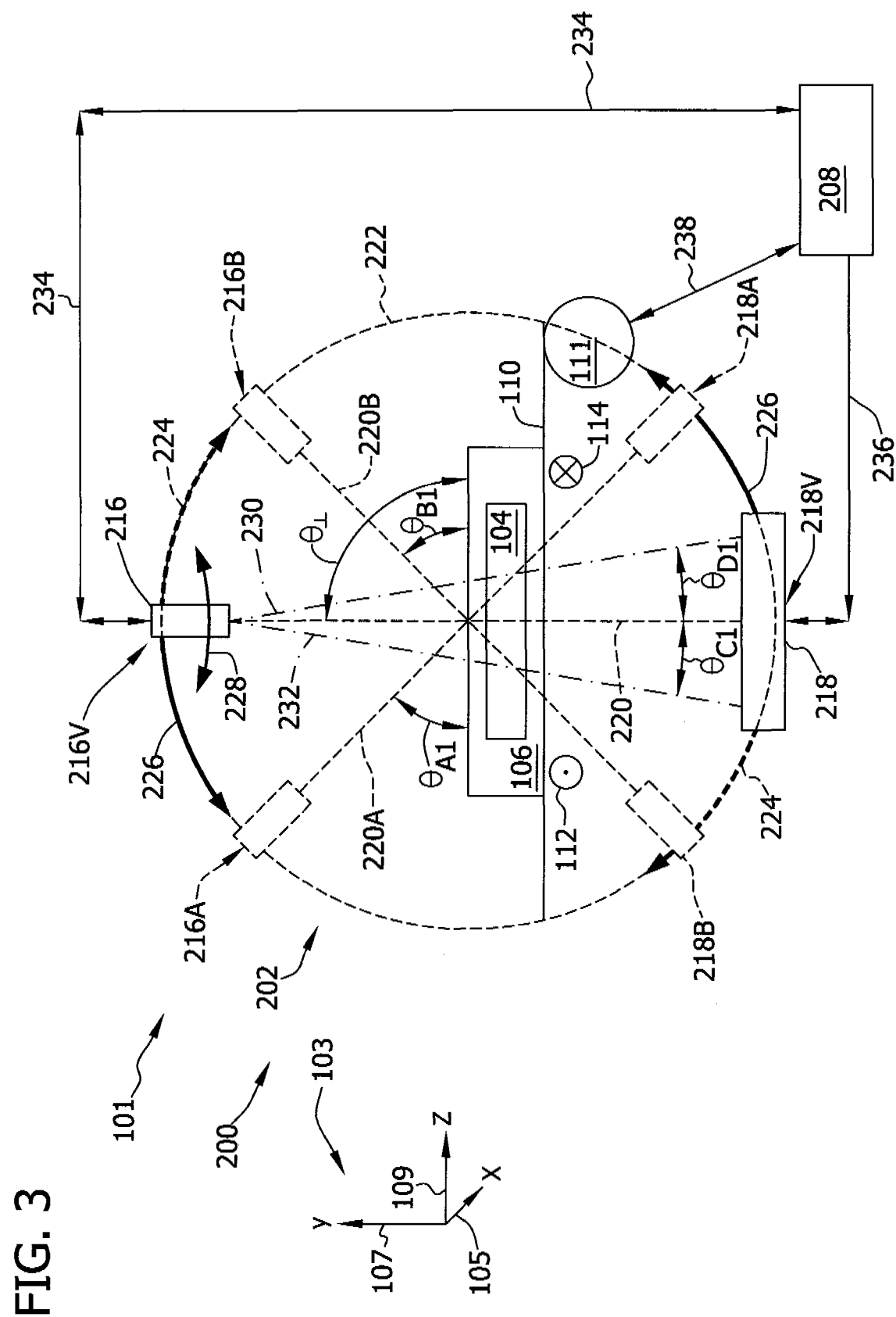

FIG. 3 is a schematic view of an alternative object imaging system 200 including an alternative x-ray laminography device 202. In a manner similar to the exemplary embodiment described above, object imaging system 200 is integrated within security system 101.

In this alternative embodiment, similar to object imaging system 100 (shown in FIG. 1), object imaging system 200 is also configured to inspect substantially flat, low-profile items that include, without limitation, laptop computer 104 that may be carried by individuals (not shown) in their associated cases 106. Moreover, in this alternative embodiment, object imaging system 200 includes a processing system 208 that is substantially similar to processing system 108 (shown in FIG. 1). Specifically, processing system 208 includes sufficient information technology resources, equipment, and programming as described above for processing system 108 to use at least one of a variety of methods of reconstruction including, but not limited to, algebraic reconstruction techniques. Such reconstruction techniques facilitate the technical effect of forming a three-dimensional (3D) image substantially representative of laptop computer 104 and case 106 and contents therein.

Also, in this alternative embodiment, processing system 208 is dedicated to object imaging system 200. Alternatively, processing system 208 may be a part of and/or integrated within one or more of, and not limited to, a larger processing system (not shown) associated with a remainder (not shown) of security system 101, a LAN, a WAN, and an Internet enabled application. Alternatively, in contrast to being a portion of a larger system, processing system 208 may be solely associated with x-ray laminography device 202.

For illustration and perspective, FIG. 3 shows coordinate system 103 that includes x-axis 105 (substantially representing the horizontal, longitudinal, or lengthwise dimension), y-axis 107 (substantially representing the vertical dimension), and z-axis 109 (substantially representing the depth, traverse, or widthwise dimension). Each axis is orthogonal to each other axis. The orientation of coordinate system 103 as shown in FIG. 3 differs from the orientation shown in FIG. 1. More specifically, x-axis 105 and z-axis 109 are exchanged to illustrate a longitudinal, or lengthwise perspective, or orientation of object imaging system 100 in FIG. 1 and a transverse, or widthwise perspective, or orientation of object imaging system 200 in FIG. 2.

Object imaging system 200 also includes traveling belt 110 and belt drive apparatus 111, both as described above. Apparatus 111 drives belt 110 primarily in the substantially longitudinal, or lengthwise direction, or orientation as indicated by direction arrow 112 substantially parallel to x-axis 105 and is shown to be exiting FIG. 3. Apparatus 111 is reversible such that belt 110 also travels with an oscillating motion in the substantially longitudinal, or lengthwise direction, or orientation as indicated by a bidirectional arrow 114 substantially parallel to x-axis 105 and is shown to be entering and exiting FIG. 3. That is, apparatus 111 drives belt 10 to travel in a direction reverse to that of arrow 112 and then drives belt 110 to travel in the direction of arrow 112 to facilitate multiple scans by x-ray laminography device 202.

In this alternative embodiment, x-ray laminography device 202 includes at least one x-ray source 216 and an array of x-ray detectors 218 that are substantially similar in design and construction to x-ray source 116 and x-ray detectors 118, respectively (both shown in FIG. 1), with the exception of physical location and operational orientation and movement within x-ray laminography device 202 as described further below. X-ray source 216 and array of x-ray detectors 218 define a first beam path 220 therebetween. Moreover, x-ray source 216 is initially positioned in a first, or vertical x-ray source position 216V and array of x-ray detectors 218 is initially positioned in a first, or vertical array of x-ray detectors position 218V such that first beam path 220 defines a radial right angle $\theta\perp$.

In this alternative embodiment, x-ray source 216 and array of x-ray detectors 218 are coupled in coordinated, joint traversal about at least a portion of a substantially circular, or a 360° travel path 222 defined by an y-z plane (not shown) defined substantially solely by y-axis 107 and z-axis 109. The traversal associated with x-ray source 216 and array of x-ray detectors 218 is contrasted to the orthogonal traversal associated with x-ray source 116 and array of x-ray detectors 118(shown in FIG. 1) defined substantially solely by x-axis 105 and y-axis 107. More specifically, in this alternative embodiment, x-ray source 216 and array of x-ray detectors 218 travel in unison in a clockwise direction as indicated by clockwise arrows 224 and a counter-clockwise direction as indicated by counter-clockwise arrows 226. Such travel may be facilitated by suitable devices known in the art including, without limitation, robotic/mechanical arms, tracks/rails, and motors (not shown).

In this alternative embodiment, travel as represented by arrows 224 and 226 is approximately 45° in each direction from the directly vertical position as shown in FIG. 2. Alternatively, travel path 222 has any shape that enables operation of object imaging system 200 and x-ray laminography device 202 as described herein, including, without limitation a parabolic shape. Also, alternatively, travel for any arcual portion of travel path 222 that enables operation of object imaging system 200 and x-ray laminography device 202 as described herein may be used. Further, alternatively, travel path 222 is defined by such traversal in a plane (not shown) that is at least partially defined by x-axis 105, y-axis 107, and z-axis 109 in any combination and proportion that enables operation of object imaging system 200 and x-ray laminography device 202 as described herein.

Moreover, x-ray source 216 and array of x-ray detectors 218 travel along circular travel path 222 such that beam path 220 substantially extends from x-ray source 216 to array of x-ray detectors 218 regardless of their position about path 222. More specifically, x-ray source 216 travels along circular path 222 per counter-clockwise arrow 226 to a second x-ray source position 216A and array of x-ray detectors 218 travels along circular travel path 222 per counter-clockwise arrow 226 to a second array of x-ray detectors position 218A such that a first oblique radial angle $\theta_{A1}$ between x-ray source 216 and case 106, as shown in FIG. 2, at least partially defines a second beam path 220A. Also, x-ray source 216 travels along circular path 222 per clockwise arrow 224 to a third x-ray source position 216B and array of x-ray detectors 218 travels along circular travel path 222 per clockwise arrow 224 to a third array of x-ray detectors position 218B such that a second oblique radial angle $\theta_{B1}$ between x-ray source 216 and case 106, as shown in FIG. 2, at least partially defines a third beam path 220B.

Further, x-ray source 216 is coupled to a pivoting device (not shown) such that pivoting action of x-ray source 216 defines an arc 228, that in this alternative embodiment, is defined in an angular range of approximately 10° to 45° in the z-y plane, that is, at least partially in the transverse direction orthogonal with bidirectional arrow 114. Alternatively, arc 228 is defined with any angular range that enables operation of object imaging system 200 and x-ray laminography device 202 as described herein. Arc 228 is defined with a larger angular range than arc 128 (shown in FIG. 1) due to the longitudinal orientation of array of x-ray detectors 218 as compared to the traverse orientation of array of x-ray detectors 118 (shown in FIG. 1). Such pivoting action subsequently defines a plurality of beam paths that includes, for example, a fourth beam path 230 and a fifth beam path 232, also in the transverse direction. Alternatively, such pivoting action defines arc 228 in a plane (not shown) that is at least partially defined by x-axis 105, y-axis 107, and z-axis 109 in any combination and proportion that enables operation of object imaging system 200 and x-ray laminography device 202 as described herein.

Moreover, such pivoting action of x-ray source 216 about arc 228 is performed within the detection constraints of array of x-ray detectors 218. That is, x-ray source 216 pivots along arc 228 such that beam paths 230 and 232 substantially extend between x-ray source 216 and x-ray detectors 218 regardless of a position of x-ray source 216 and a position of x-ray detectors 218 about path 222. Such pivoting action about arc 228 in conjunction with the circular traversal about path 222 facilitates greater flexibility of scanning, or illuminating case 106 and laptop computer 104 at varying radially oblique angles that include, but are not limited to, a third oblique radial angle $\theta_{C1}$ and a fourth oblique radial angle $\theta_{D1}$. Angles $\theta_{C1}$ and $\theta_{D1}$ are at least partially defined by x-ray source 216 and laptop computer 104 and case 106, and both angles $\theta_{C1}$ and $\theta_{D1}$ are at least partially defined by arc 228. Such pivoting action facilitates greater scanning resolution as discussed further below.

Further, such pivoting action of x-ray source 216 facilitates reducing traversing movements of x-ray source 216 about arrows 224 and 226 and oscillating travel of belt 110 via apparatus 111, thereby facilitating extending an expected operational lifetime of those components associated with such traversing and oscillating and decreasing a period of time associated with scanning of computer 104 and case 106.

Moreover, reducing such traversing and oscillating facilitates use of smaller components, thereby facilitating decreasing a footprint of object imaging system 200 and x-ray laminography device 202.

In this alternative embodiment, processing system 208 is coupled with components of object imaging system 200 including x-ray source 216, array of x-ray detectors 218, and belt drive apparatus 111 via communication conduits 234, 236, and 238, respectively. Processing system 208 substantially controls and coordinates operation of x-ray source 216, x-ray detectors 218, and apparatus 111 to illuminate laptop computer 104 and case 106 with the x-ray beam as described herein.

Referring again to FIG. 2, exemplary method 150 of operating security system 101 (shown in FIG. 3) includes directing 152 coordinated traversal of at least one x-ray detector 218 and at least one x-ray source 216 about an object, such as laptop computer 104, along travel path 222 at least partially defined radially about laptop computer 104. Method 150 also includes illuminating 154 laptop computer 104 with x-rays directed from a plurality of oblique radial angles $\theta_{A1}$ and $\theta_{B1}$ defined between x-ray source 216 and laptop computer 104.

Method 150 further includes defining 156 at least one x-ray beam path 220, 220A, and 220B between at least one x-ray source 216 and at least one x-ray detector 218, wherein the at least one x-ray beam path 220, 220A, and 220B is at least partially defined by at least one of plurality of oblique radial angles $\theta_{A1}$ and $\theta_{B1}$. Method 150 also includes pivoting 158 at least one x-ray source 216, thereby defining pivot arc 228, wherein the at least one x-ray beam path includes plurality of x-ray beam paths 230 and 232 at least partially defined by the pivot arc 228.

Method 150 further includes at least partially 162 defining plurality of oblique radial angles $\theta_{A1}$, $\theta_{B1}$, $\theta_{C1}$, and $\theta_{D1}$ in a transverse direction with respect to direction of travel 114 of traveling belt 110. Moreover, in method 150, positioning 160 laptop computer 104 on traveling belt 110 comprises oscillating 164 traveling belt 110 in a longitudinal dimension, or x-axis 105.

Operation of object imaging system 200 and x-ray laminography device 202 is substantially similar to that described for object imaging system 100 and x-ray laminography device 102 above (all shown in FIG. 1).

Figure 4:
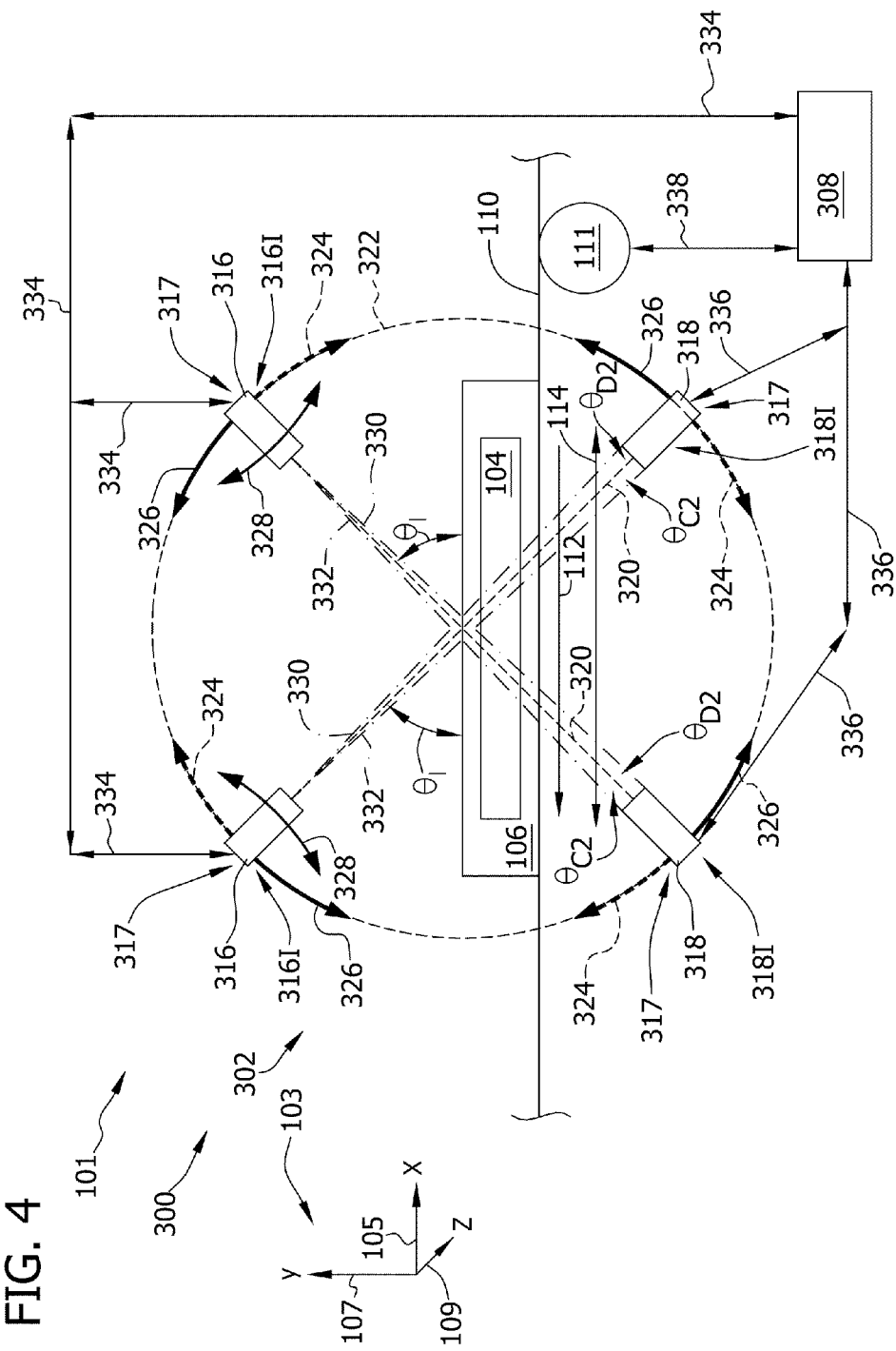

FIG. 4 is a schematic view of another alternative object imaging system 300 including another alternative x-ray laminography device 302. In a manner similar to the embodiments described above, object imaging system 300 is integrated within a larger, more comprehensive security system 101.

In this alternative embodiment, similar to object imaging systems 100 and 200 (shown in FIGS. 1 and 3, respectively), object imaging system 300 is also configured to inspect substantially flat, low-profile items that include, without limitation, laptop computers 104 that may be carried by individuals (not shown) in their associated cases 106. Moreover, in this alternative embodiment, object imaging system 300 includes a processing system 308 that is substantially similar to processing systems 108 and 208 (shown in FIGS. 1 and 3, respectively). Specifically, processing system 308 includes sufficient information technology resources, equipment, and programming as described above for processing system 108 to use at least one of a variety of methods of reconstruction including, but not limited to, algebraic reconstruction techniques. Such reconstruction techniques facilitate the technical effect of forming a three-dimensional (3D) image substantially representative of laptop computer 104 and case 106 and contents therein.

Also, in this alternative embodiment, processing system 308 is dedicated to object imaging system 300. Alternatively, processing system 308 may be a part of and/or integrated within one or more of, and not limited to, a larger processing system (not shown) associated with a remainder (not shown) of security system 101, a LAN, a WAN, and an Internet enabled application. Alternatively, in contrast to being a portion of a larger system, processing system 308 may be solely associated with x-ray laminography device 302.

For illustration and perspective, FIG. 4 shows coordinate system 103 that includes x-axis 105 (substantially representing the horizontal, longitudinal, or lengthwise dimension), y-axis 107 (substantially representing the vertical dimension), and z-axis 109 (substantially representing the depth, traverse, or widthwise dimension). Each axis is orthogonal to each other axis. The orientation of coordinate system 103 as shown in FIG. 4 is substantially similar to the orientation shown in FIG. 1.

Object imaging system 300 also includes traveling belt 110 and belt drive apparatus 111, both as described above. Apparatus 111 drives belt 110 primarily in the substantially longitudinal, or lengthwise direction, or orientation as indicated by direction arrow 112 substantially parallel to x-axis 105. Apparatus 111 is reversible such that belt 110 also travels with an oscillating motion in the substantially longitudinal, or lengthwise direction, or orientation as indicated by a bidirectional arrow 114 substantially parallel to x-axis 105. That is, apparatus 111 drives belt 110 to travel in a direction reverse to that of arrow 112 and then drives belt 110 to travel in the direction of arrow 112 to facilitate multiple scans by x-ray laminography device 302.

In this alternative embodiment, x-ray laminography device 302 includes a plurality of x-ray sources 316 and a plurality of arrays of x-ray detectors 318 that are substantially similar to x-ray source 116 and x-ray detectors 118, respectively (both shown in FIG. 1). In this alternative embodiment, each x-ray source 316 and each array of x-ray detectors 318 defines a x-ray source/detector pair 317. Also, in this alternative embodiment, there are two x-ray source/detector pairs 317. Alternatively, x-ray laminography device 302 includes any suitable number of x-ray source/detector pairs 317 that enables operation of object imaging system 300 and x-ray laminography device 302 as described herein. Such x-ray source/detector pairs 317 are contrasted to x-ray source 216 and array of x-ray detectors 218 (shown in FIG. 3) and x-ray source 116 and array of x-ray detectors 118 (shown in FIG. 1).

In this alternative embodiment, each x-ray source/detector pair 317 is substantially symmetrical with each other x-ray source/detector pair 317 about circular travel path 322. That is, each x-ray source/detector pair 317 defines a substantially similar first beam path 320 therebetween. Moreover, each x-ray source 316 is initially positioned in a substantially similar initial x-ray source position 316I and each array of x-ray detectors 318 is initially positioned in a substantially similar initial array of x-ray detectors position 318I such that each first beam path 320 defines a substantially similar first, or initial oblique radial angle $\theta_I$. Alternatively, each x-ray source/detector pair 317 is positioned substantially asymmetrically with each other x-ray source/detector pair 317 about circular travel path 322, thereby defining a plurality of unique and distinct x-ray source positions, array of x-ray detectors positions, and initial oblique radial angles (neither shown).

In this alternative embodiment, each of x-ray source 316 and array of x-ray detectors 318, or pair 317, are further coupled in coordinated, joint traversal about at least a portion of a substantially circular, or a 360° travel path 322 defined by an x-y plane (not shown) defined substantially solely by x-axis 105 and y-axis 107. More specifically, in this alternative embodiment, each x-ray source 316 and array of x-ray detectors 318 arranged in each pair 317 travel in unison in a clockwise direction as indicated by clockwise arrows 324 and a counter-clockwise direction as indicated by counter-clockwise arrows 326. Such travel is facilitated by suitable devices known in the art including, without limitation, robotic/mechanical arms, tracks/rails, and motors (not shown).

In this alternative embodiment, travel represented by arrows 324 and 326 is approximately 22.5° in each direction from the approximately 22.5° position away from directly vertical as shown in FIG. 4. Alternatively, travel path 322 has any shape that enables operation of object imaging system 300 and x-ray laminography device 302 as described herein, including, without limitation, a parabolic shape. Also, alternatively, travel for any arcual portion of travel path 322 that enables operation of object imaging system 300 and x-ray laminography device 302 as described herein may be used. Further, alternatively, travel path 322 is defined by such traversal in a plane (not shown) that is at least partially defined by x-axis 105, y-axis 107, and z-axis 109 in any combination and proportion that enables operation of object imaging system 300 and x-ray laminography device 302 as described herein.

Moreover, each x-ray source/detector pair 317 travels along circular travel path 322 such that beam path 320 substantially extends from each associated x-ray source 316 to each associated x-ray detector 318 regardless of their position about path 322. More specifically, each x-ray source/detector pair 317 travels along circular travel path 322 such that touching and/or collisions of x-ray sources 316 and x-ray detectors 318 with each other is substantially prevented. Each x-ray source/detector pair 317 travels along circular path 322 per counter-clockwise arrows 326 to a second x-ray source/detector pair position (not shown) similar to positions 116A and 216A (shown in FIGS. 1 and 3, respectively). Further, such position facilitates defining a second oblique radial angle (not shown) between x-ray source 316 and case 106 similar to angles $\theta_A$ and $\theta_{A1}$ (shown in FIGS. 1 and 3, respectively). Moreover, the second oblique radial angle at least partially defines a second beam path (not shown) similar to second beam paths 120A and 220A (shown in FIGS. 1 and 3, respectively).

Each x-ray source/detector pair 317 travels along circular travel path 322 per clockwise arrow 324 to a third x-ray source/detector pair position (not shown) similar to positions 116B and 216B (shown in FIGS. 1 and 3, respectively). Further, the position facilitates defining a third oblique radial angle (not shown) between x-ray source 316 and case 106 similar to angles $\theta_B$ and $\theta_{B1}$ (shown in FIGS. 1 and 3, respectively). Moreover, the third oblique radial angle at least partially defines a third beam path (not shown) similar to third beam paths 120B and 220B (shown in FIGS. 1 and 3, respectively).

Each x-ray source 316 is coupled to a pivoting device (not shown) such that pivoting action of x-ray source 316 defines an arc 328 that, in this alternative embodiment, is defined in an angular range of approximately 2° to 10° in the x-y plane. Alternatively, arc 328 is defined with any angular range that enables operation of object imaging system 300 and x-ray laminography device 302 as described herein. Arc 328 is defined with a similar angular range as that of arc 128 (shown in FIG. 1) due to the traverse orientation of array of x-ray detectors 318 as compared to the longitudinal orientation of array of x-ray detectors 218. Such pivoting action subsequently defines a plurality of beam paths that includes, for example, a plurality of fourth beam paths 330 and a plurality of fifth beam paths 332, also in the x-y plane. Alternatively, such pivoting action defines arc 328 in a plane (not shown) that is at least partially defined by x-axis 105, y-axis 107, and z-axis 109 in any combination and proportion that enables operation of object imaging system 300 and x-ray laminography device 302 as described herein.

Moreover, such pivoting action of each x-ray source 316 about arc 328 is performed within the detection constraints of each associated array of x-ray detectors 318. That is, each x-ray source 316 pivots along arc 328 such that associated paths 330 and 332 substantially extend between each associated x-ray source 316 and x-ray detectors 318 regardless of a position of x-ray source 316 and a position of x-ray detectors 318 about path 322. Such pivoting action about arc 328 in conjunction with the circular traversal about path 322 facilitates greater flexibility of scanning, or illuminating case 106 and laptop computer 104 at varying radially oblique angles that include, but are not limited to, a fourth oblique radial angle $\theta_{C2}$ and a fifth oblique radial angle $\theta_{D2}$. Fourth $\theta_{C2}$ and fifth $\theta_{D2}$ oblique radial angles are at least partially defined by x-ray source 316 and case 106, as shown in FIG. 4, and both fourth $\theta_{C2}$ and fifth $\theta_{D2}$ angles are at least partially defined by arc 328. Such pivoting action facilitates greater scanning resolution.

Further, such pivoting action of x-ray source 316 facilitates reducing traversing movements of x-ray source 316 about arrows 324 and 326 and oscillating travel of belt 110 via apparatus 111, thereby facilitating extending an expected operational lifetime of those components associated with such traversing and oscillating and decreasing a period of time associated with scanning of computer 104 and case 106. Moreover, reducing such traversing and oscillating facilitates use of smaller components, thereby facilitating decreasing a footprint of object imaging system 300 and x-ray laminography device 302.

In this alternative embodiment, processing system 308 is coupled with components of object imaging system 300 that include, but are not limited to, each x-ray source 316, each array of x-ray detectors 318, and belt drive apparatus 111 via communication conduits 334, 336, and 338, respectively. Processing system 308 substantially controls and coordinates operation of x-ray sources 316, x-ray detectors 318, and apparatus 111 to illuminate laptop computer 104 and case 106 with a plurality of x-ray beams as described herein. Moreover, in this alternative embodiment, processing system 308 facilitates movement of x-ray source/detector pairs 317 to substantially reduce mutual interference between pairs 317.

Referring again to FIG. 2, exemplary method 150 of operating security system 101 (shown in FIG. 4) includes directing 152 coordinated traversal of at least one x-ray detector 318 and at least one x-ray source 316 about an object, such as laptop computer 104, along travel path 322 at least partially defined radially about laptop computer 104. Method 150 also includes illuminating 154 laptop computer 104 with x-rays directed from a plurality of oblique radial angles $\theta_1$ defined between x-ray sources 316 and laptop computer 104.

Method 150 further includes defining 156 at least one x-ray beam path 320 between at least one x-ray source 316 and at least one x-ray detector 318, wherein the at least one x-ray beam path 320 is at least partially defined by at least one of plurality of oblique radial angles $\theta_T$. Method 150 also includes pivoting 158 at least one x-ray source 316, thereby defining pivot arc 328, wherein the at least one x-ray beam path includes plurality of x-ray beam paths 330 and 332 at least partially defined by the pivot arc 328.

Method 150 further includes at least partially 162 defining plurality of oblique radial angles $\theta_{C2}$, and $\theta_{D2}$ in a transverse or longitudinal direction with respect to direction of travel 114 of traveling belt 110. Moreover, in method 150, positioning 160 laptop computer 104 on traveling belt 110 comprises oscillating 164 traveling belt 110 in a longitudinal dimension, or x-axis 105.

Method 150 also includes illuminating 166 laptop computer 104 with x-rays directed from plurality of x-ray sources 316, thereby defining plurality of x-ray beam paths 320, 330, and 332.

Operation of object imaging system 300 and x-ray laminography device 302 is substantially similar to that described above for object imaging systems 100 and 200 and x-ray laminography devices 102 and 202 (all shown in FIGS. 1 and 3, respectively).

Moreover, object imaging system 300 and x-ray laminography device 302 represent use of a plurality of x-ray source/detector pairs 317 with substantially the embodiment shown in FIG. 3. The embodiment shown in FIG. 4 may also include a plurality of x-ray sources 216 and arrays of x-ray detectors 218 (both shown in FIG. 3) to form x-ray source/detector pairs in a manner similar to that associated with x-ray source/detector pairs 317.

The above-described method and x-ray laminography devices facilitate effective and efficient operation of security systems. The security systems include an x-ray laminography device that scans substantially flat, low-profile items, such as laptop computers, from a variety of oblique scanning angles. The x-ray laminography device subsequently generates and displays a three-dimensional (3D) image of the contents of the items within an associated case. The x-ray laminography device decreases a need to have items, such as laptop computers, removed from their cases at security checkpoints, thereby decreasing efforts of screening agencies and individuals and the time per unit item expended. Moreover, the x-ray laminography devices described herein include a small foot print such that integration of the devices with existing security systems is facilitated. Also, the method and x-ray laminography devices described herein facilitate subjecting moving components to minimal motion, and associated wear that is necessary to generate a satisfactory 3D image of a low-profile item.

Exemplary embodiments of methods and x-ray laminography devices associated with operating a security system are described above in detail. The methods and x-ray laminography devices are not limited to the specific embodiments described herein, but rather, components of systems and/or steps of the methods may be utilized independently and separately from other components and/or steps described herein. For example, the methods may also be used in combination with other security systems and methods, and are not limited to practice with only the security systems as described herein. Rather, the exemplary embodiment can be implemented and utilized in connection with many other security system applications.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An x-ray laminography device, comprising:
a traveling belt;
at least one x-ray detector; and
at least one x-ray source coupled in coordinated traversal with said at least one x-ray detector, said at least one x-ray source configured to generate and transmit x-rays, said at least one x-ray detector and said at least one x-ray source configured to traverse an at least partially radial travel path in unison about an object, the object is illuminated with x-rays from a plurality of oblique radial angles defined between said at least one x-ray source and the object, the oblique radial angles at least partially defined in a longitudinal direction and a transverse direction with respect to a direction of travel of said traveling belt.

2. An x-ray laminography device in accordance with claim 1, wherein said at least one x-ray source and said at least one x-ray detector cooperate to define at least one x-ray beam path therebetween, and said at least one x-ray beam path is at least partially further defined by at least one of the plurality of oblique radial angles.

3. An x-ray laminography device in accordance with claim 2, wherein said at least one x-ray source defines a pivot arc that at least partially defines a plurality of x-ray beam paths.

4. An x-ray laminography device in accordance with claim 3, wherein said at least one x-ray source and said at least one x-ray detector comprise a plurality of x-ray sources and a plurality of x-ray detectors that define a plurality of x-ray source/detector pairs, and each of said plurality of x-ray source/detector pairs define at least one x-ray beam path, each of said plurality of x-ray source/detector pairs are substantially similar.

5. An x-ray laminography device in accordance with claim 4, wherein said plurality of x-ray source/detector pairs define a plurality of x-ray beam paths that are at least partially defined by the plurality of oblique radial angles, and each of the plurality of oblique radial angles is at least partially defined by at least one of a longitudinal orientation of said x-ray laminography device and a transverse orientation of said x-ray laminography device.

6. An object imaging system, comprising:
at least one processing system;
a traveling belt operatively coupled to said at least one processing system; and
an x-ray laminography device comprising:
a plurality of x-ray detectors coupled to said at least one processing system; and
a plurality of x-ray sources coupled in coordinated traversal with said plurality of x-ray detectors to define a plurality of x-ray source/detector pairs, each of said x-ray source/detector pairs defining an x-ray beam path therebetween, each of said plurality of x-ray sources configured to generate and transmit x-rays within the plurality of x-ray beam paths defined by each of said plurality of x-ray source/detector pairs, said plurality of x-ray source/detector pairs configured to traverse an at least partially radial travel path in unison about an object, the object is illuminated with x-rays from a plurality of oblique radial angles defined between said plurality of x-ray sources and the object, the oblique radial angles at least partially defined in a longitudinal direction and a transverse direction with respect to a direction of travel of said traveling belt.

7. An object imaging system in accordance with claim 6, wherein the plurality of x-ray beam paths are at least partially further defined by at least one of the plurality of oblique radial angles.

8. An object imaging system in accordance with claim 7, wherein each of said plurality of x-ray sources defines a pivot arc that at least partially further defines the plurality of x-ray beam paths.

9. An object imaging system in accordance with claim 6, wherein said plurality of x-ray source/detector pairs define the plurality of x-ray beam paths such that each of the plurality of oblique radial angles is at least partially further defined by at least one of a longitudinal orientation of said x-ray laminography device and a transverse orientation of said x-ray laminography device.

10. An object imaging system in accordance with claim 6, further comprising at least one belt drive apparatus coupled to said traveling belt, and said at least one belt drive apparatus is operatively coupled to said at least one processing system.

11. An object imaging system in accordance with claim 10, wherein said at least one belt drive apparatus oscillates said traveling belt.

12. An object imaging system in accordance with claim 10, wherein said at least one belt drive apparatus and said plurality of x-ray source/detector pairs cooperate to illuminate the object with x-rays, the object having a flat low-profile with respect to at least a portion of said traveling belt the object rests upon.

13. A method for operating a security system, said method comprising:
   conveying an object along a travel path on a traveling belt;
   directing coordinated traversal of a plurality of x-ray detectors and a plurality of x-ray sources about the object along the travel path at least partially defined radially about the object; and
   illuminating the object with x-rays directed from a plurality of oblique radial angles at least partially defined between the plurality of x-ray sources and the object in a longitudinal direction and a transverse direction with respect to a direction of travel of the traveling belt, thereby at least partially defining a plurality of x-ray beam paths.

14. A method in accordance with claim 13, wherein illuminating the object with x-rays directed from a plurality of oblique radial angles at least partially defined between the plurality of x-ray sources and the object comprises at least one of:
   illuminating the object via the plurality of x-ray beam paths defined between the plurality of x-ray sources and the plurality of x-ray detectors, wherein each of the plurality of x-ray beam paths are at least partially further defined by at least one of the plurality of oblique radial angles; and
   pivoting the at least one x-ray source, thereby defining a pivot arc, wherein the plurality of x-ray beam paths defined between the plurality of x-ray sources and the plurality of x-ray detectors further partially define the plurality of x-ray beam paths at least partially defined by the pivot arc.

15. A method in accordance with claim 13, further comprising positioning the object on the traveling belt.

16. A method in accordance with claim 15, wherein positioning the object on the traveling belt comprises oscillating the traveling belt in a longitudinal dimension.

* * * * *